(12) United States Patent
Sharma et al.

(10) Patent No.: US 7,437,958 B2
(45) Date of Patent: Oct. 21, 2008

(54) STERILE SINGLE USE SAMPLING DEVICE

(75) Inventors: Pramod K. Sharma, Willoughby, OH (US); Susan G. Quick, Kirtland, OH (US); Karl F. Ludwig, II, Girard, PA (US)

(73) Assignee: American Sterilizer Company, Mentor, OH (US)

( * ) Notice: Subject to any disclaimer, the term of this patent is extended or adjusted under 35 U.S.C. 154(b) by 291 days.

(21) Appl. No.: 11/358,382

(22) Filed: Feb. 21, 2006
(Under 37 CFR 1.47)

(65) Prior Publication Data

US 2007/0193376 A1    Aug. 23, 2007

(51) Int. Cl.
*G01N 1/14* (2006.01)
(52) U.S. Cl. .................................. 73/863.84
(58) Field of Classification Search ............... 73/863.84
See application file for complete search history.

(56) References Cited

U.S. PATENT DOCUMENTS

| | | | |
|---|---|---|---|
| 3,906,935 A | 9/1975 | Raia et al. ..................... 128/2 |
| 3,952,729 A * | 4/1976 | Libman et al. ............... 600/575 |
| 4,010,648 A | 3/1977 | Harris, Sr. et al. ............. 73/423 |
| 4,423,641 A | 1/1984 | Ottung ..................... 73/863.86 |
| 5,095,765 A | 3/1992 | Filbey et al. ............. 73/863.56 |
| 5,135,492 A * | 8/1992 | Melker et al. ................ 604/508 |
| 5,342,316 A * | 8/1994 | Wallace .................. 604/167.02 |
| 5,433,120 A | 7/1995 | Boyd et al. ............. 73/863.81 |
| 5,600,075 A | 2/1997 | Peterson .................. 73/863.71 |
| 5,743,886 A * | 4/1998 | Lynn et al. .................. 604/191 |
| 5,907,110 A | 5/1999 | Garcia et al. ............. 73/864.74 |
| 6,032,543 A * | 3/2000 | Arthun .................... 73/863.84 |
| 2003/0139688 A1* | 7/2003 | Lamoureux et al. ......... 600/578 |

* cited by examiner

*Primary Examiner*—Robert R Raevis
(74) *Attorney, Agent, or Firm*—Kusner & Jaffe; Michael A. Centanni

(57) ABSTRACT

The present invention provides a device for obtaining a sample of fluid from a process conduit. The device includes a tubular core that has a passageway extending therethrough. The tubular core has ends that are attachable to spaced-apart portions of a conduit. A tubular sleeve surrounds the tubular core such that the tubular core extends lengthwise through the tubular sleeve. The tubular sleeve has a boss formed thereon that has a bore extending therethrough. The bore fluidly communicates with the tubular core. A syringe is mountable to the boss and the syringe has a needle. The needle is dimensioned to extend through the bore to puncture the core and to project into the passageway inside the core.

12 Claims, 5 Drawing Sheets

STERILE SINGLE USE SAMPLING DEVICE

FIELD OF THE INVENTION

The present invention relates to the art of obtaining fluid samples from a process conduit, and more particularly, to a method and apparatus for obtaining sterile fluid samples from a decontamination system.

BACKGROUND OF THE INVENTION

Many processes require sterile samples of a fluid to be obtained from within a process conduit without either the sample or the fluid within the conduit being contaminated with biological activity. Processes that may require such sterile sampling include microbiological and chemical monitoring, biopharmaceutical manufacturing, other chemical processes, and decontamination systems.

Verification of whether a decontamination process was effective is important for the sterilization of medical instruments. A typical decontamination process consists of a treatment/decontamination cycle or cycles followed by a rinse cycle or cycles using sterile water. Whether a decontamination process is successful may be determined by assessing the degree to which any biological activity exists in the rinse water. In this respect, samples of the rinse water from the final rinse cycle may be obtained and incubated to determine whether the rinse water contains any biological activity. If the sample of rinse water contains biological activity, it may be assumed that the decontamination cycle was ineffective. If the sampling method introduces biological activity or contamination into the sample, then misleading results may be obtained. Obtaining a liquid sample without introducing any biological activity into the sample is therefore essential to determining whether a decontamination process was effective.

Fluid samples may be taken from a conduit to be sampled by many methods. A typical apparatus for obtaining sterile samples provides valves that allow a sample to be withdrawn from a conduit and then allow the conduit to be resealed without contaminating the conduit. One problem with these systems is that they require flushing in order to maintain sterility.

The present invention overcomes this and other problems and provides an assembly to be installed within a system conduit for obtaining, under sterile conditions, a fluid sample from a process stream within the conduit.

SUMMARY OF THE INVENTION

In accordance with the present invention, there is provided a device for obtaining a sample of fluid from a process conduit. The device includes a tubular core that has a passageway extending therethrough. The tubular core has ends that are attachable to spaced-apart portions of a process conduit. A tubular sleeve surrounds the tubular core such that the tubular core extends lengthwise through the tubular sleeve. The tubular sleeve has a bore extending therethrough that fluidly communicates with the tubular core. A syringe having a needle is mountable to the sleeve. The needle is dimensioned to extend through the bore to puncture the core and to project into the passageway inside the core.

An advantage of the present invention is a device for obtaining a fluid sample from a conduit.

Another advantage of the present invention is a device as described above that obtains a sample from a conduit under sterile conditions.

Another advantage of the present invention is a device as described above for obtaining a sterile sample from a conduit that does not contaminate the conduit.

Another advantage of the present invention is a device as defined above that is removable from the conduit.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
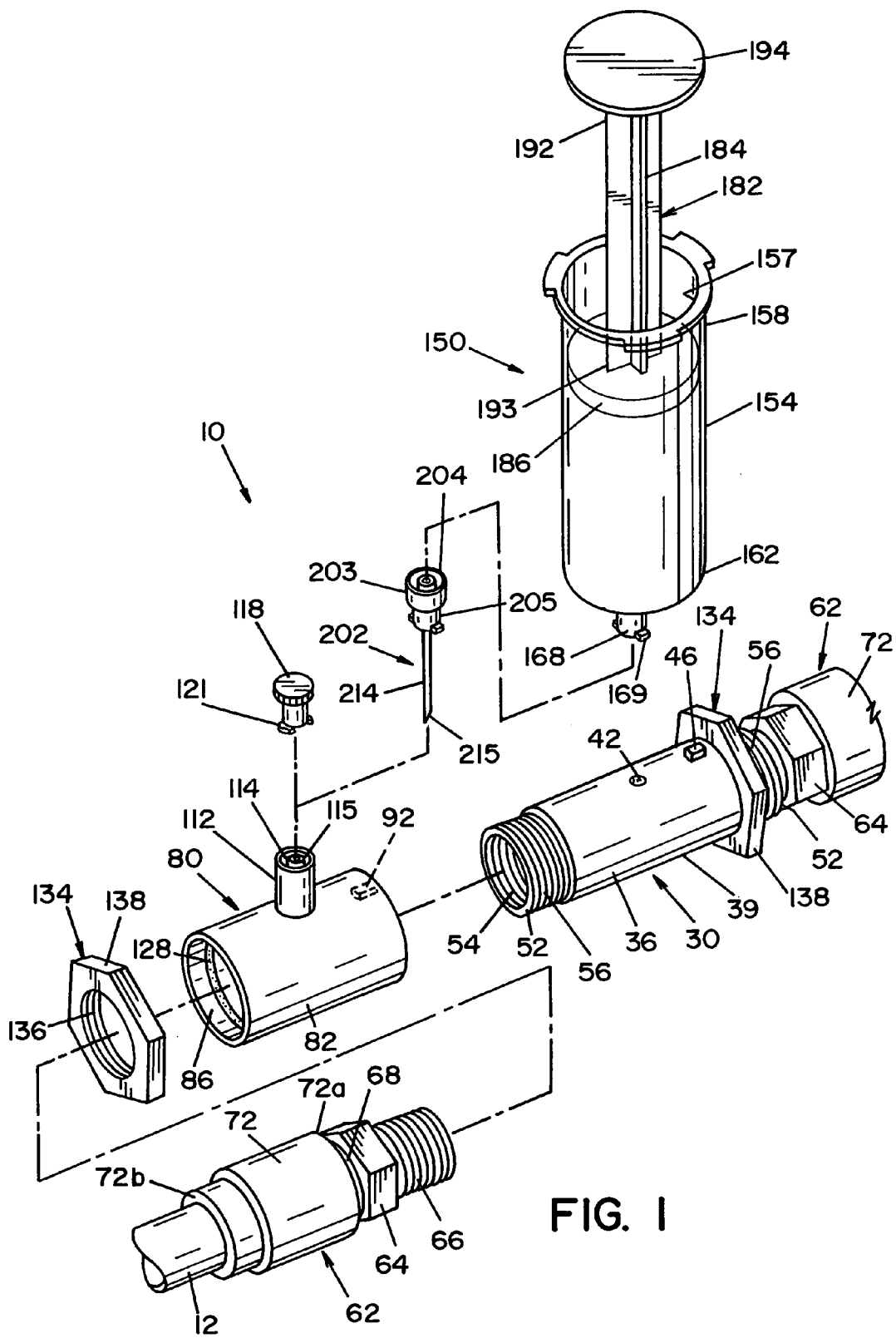
FIG. 1 is an exploded view of a sterile sampling assembly illustrating a preferred embodiment of the present invention.
Figure 2:
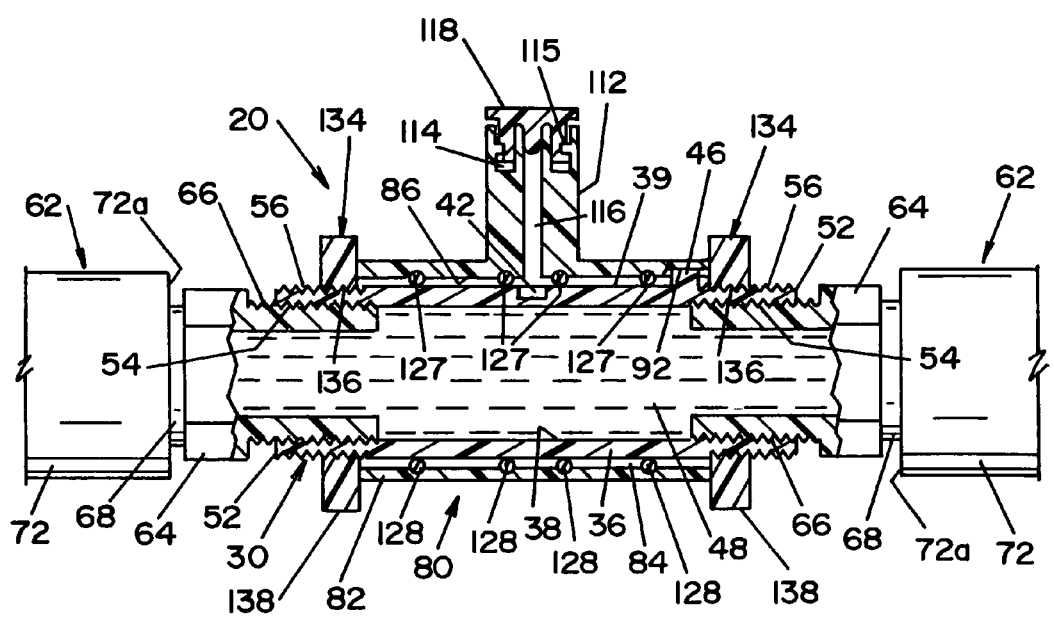
FIG. 2 is a sectional view of the sterile sampling assembly shown in FIG. 1, showing the assembly installed within a process conduit.

Referring now to the drawings wherein the showings are for the purposes of illustrating a preferred embodiment of the present invention only and not for the purposes of limiting same, a sampling device 10 for withdrawing a fluid sample from within a conduit without contaminating fluid within the conduit is shown. FIG. 1 shows an exploded view of sterile sampling device 10 and a process conduit 12. FIG. 2 shows a sectional view of a portion of sterile sampling device 10 after installation in process conduit 12. Broadly stated, device 10 is comprised of a body assembly 20 and a syringe 150.

Body assembly 20 includes a core 30 and a housing 80. As best seen in FIGS. 1 and 2, core 30 is an elongated, tubular, element that has a cylindrical wall 36. Wall 36 has an interior surface 38 that defines a first passageway 48. First passageway 48 extends axially through core 30 and is dimensioned to allow flow of a process fluid therethrough. Wall 36 has an outer surface 39. A recess 42 is formed in outer surface 39 of wall 36. Recess 42 defines a thinner area or region relative to the remainder of wall 36. As shall be described in greater detail below, recess 42 defines an area in wall 36 that is dimensioned to facilitate puncture or penetration of core 30 by syringe 150.

In the illustrated embodiment, a generally rectangular projection 46 is formed on outer surface 39 at one end of core 30. Core 30 has two ends, each designated 52 that are each formed to have interior threads 54 and exterior threads 56. It is contemplated that the connection made by interior threads 54 and exterior threads 66 is formed as a flair fitting (not shown). An exterior threaded feature designed to accept a flare nut would be located on core 30 such that no threaded connections are exposed to first passageway 48. The flair nut would be free to rotate in order to establish a threaded connection between a coupling 62 and core 30. Interior threads 54 are dimensioned to receive coupling 62. Coupling 62 includes a hexagonally shaped connector 64. Connector 64 has a first threaded end 66 dimensioned to threadably engage interior threads 54 of core 30. Connector 64 has a second end 68 that is rotatably attached to a first end 72a of a collar 72. A second end 72b of collar 72 is dimensioned to be attached to a conduit 12.

Housing 80 is a generally tubular sleeve that has a wall 82. In the embodiment shown, wall 82 is cylindrical in shape and has an inner surface 86. Inner surface 86 defines an opening 84 that is dimensioned to receive core 30. As shown in the drawings, housing 80 is dimensioned such that an annular gap exists between inner surface 86 of housing 80 and outer surface 39 of core 30. A rectangular recess 92 is formed in inner surface 86 of housing 80 at one end thereof. Recess 92 is dimensioned to receive projection 46 of core 30.

Housing 80 is dimensioned to receive core 30 such that core 30 extends axially through housing 80 and projection 46 of core 30 engages recess 92 of housing 80. Together projection 46 and recess 92 are operable to prevent housing 80 from moving radially relative to core 30. Exterior threads 56 of core 30 are dimensioned to receive a pair of compression nuts 134 illustrated in FIG. 2. Compression nuts 134 have interior threads 136 and a hexagonally shaped outer surface 138, as is conventionally known. Pair of compression nuts 134 are operable to engage exterior threads 56 such that core 30 is retained axially within opening 84 of housing 80.

Housing 80 has a generally cylindrical boss 112 projecting radially from wall 82. Boss 112 is preferably integrally formed as part of housing 80. An annular recess 114 is formed at an end of boss 112. Annular recess 114 has a surface engaging means 115 formed therein. In a preferred embodiment, surface engaging means 115 is dimensioned to receive a fitting formed as a male Luer-Lok® fitting. A cylindrical bore 116 extends through boss 112 and is fluidly connected with opening 84. A cap 118 is provided for attachment to boss 112. Cap 118 has a surface means 121 formed thereon to matingly engage surface engaging means 115 of boss 112 to facilitate attachment of cap 118 to boss 112. In the embodiment shown, surface means 121 is a male Luer-Lok® fitting. Boss 112 is disposed on housing 80 relative to recess 92 of housing 80 such that, when rectangular projection 46 is engaged with rectangular recess 92, bore 116 is aligned with recess 42 of core 30.

In the illustrated embodiment, inner surface 86 of wall 82 has a plurality of annular grooves 127 defined therein that are dimensioned to retain a plurality of o-rings 128. O-rings 128 are circumferentially disposed between core 30 and housing 80 on both sides of recess 42, as shown in FIG. 2. O-rings 128 are dimensioned to form a fluid-tight seal between inner surface 86 of housing 80 and outer surface 39 of core 30.

Figure 4:
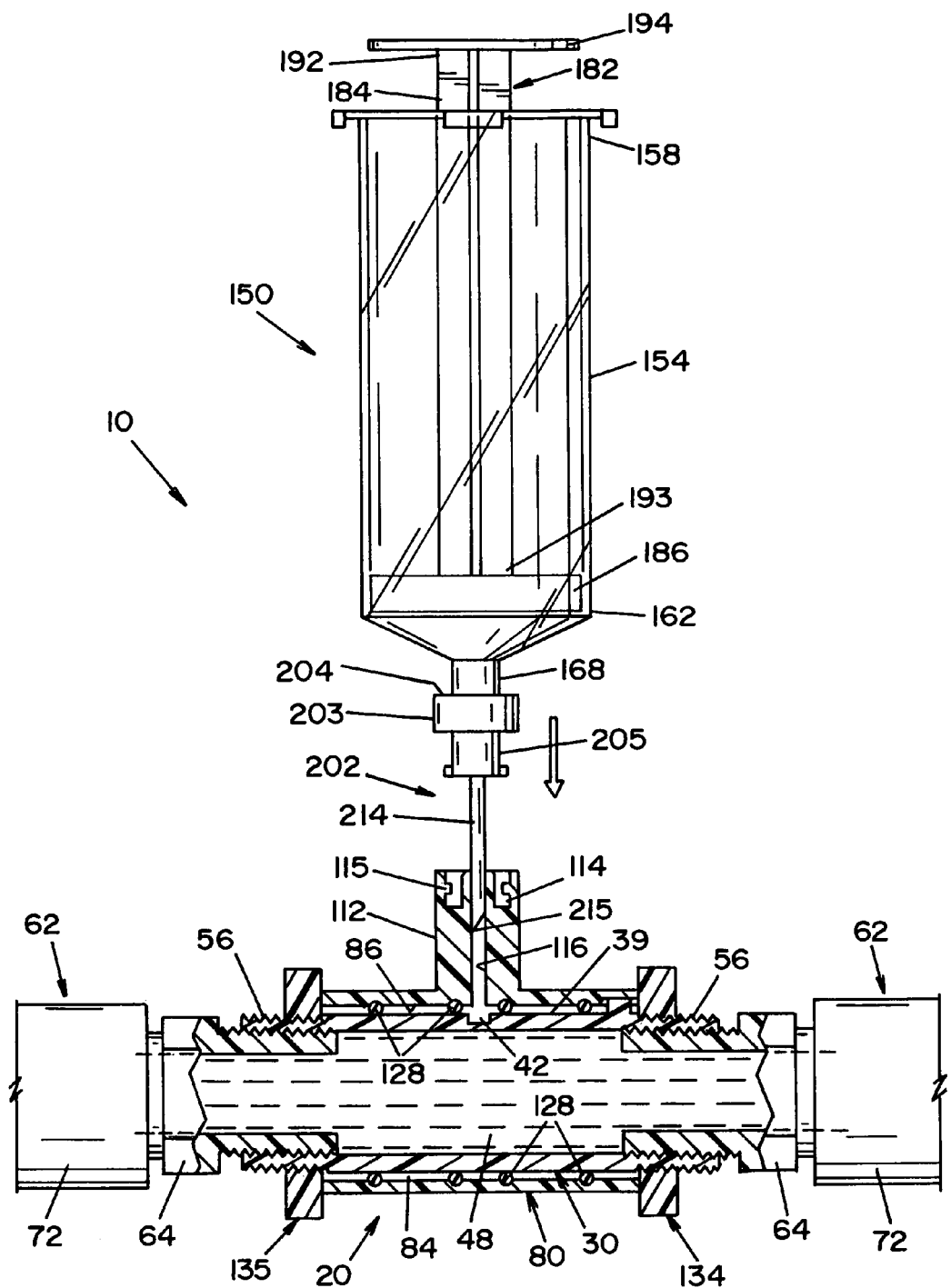
FIG. 4 is an enlarged sectioned view taken along lines 4-4 of FIG. 3.
Figure 5:
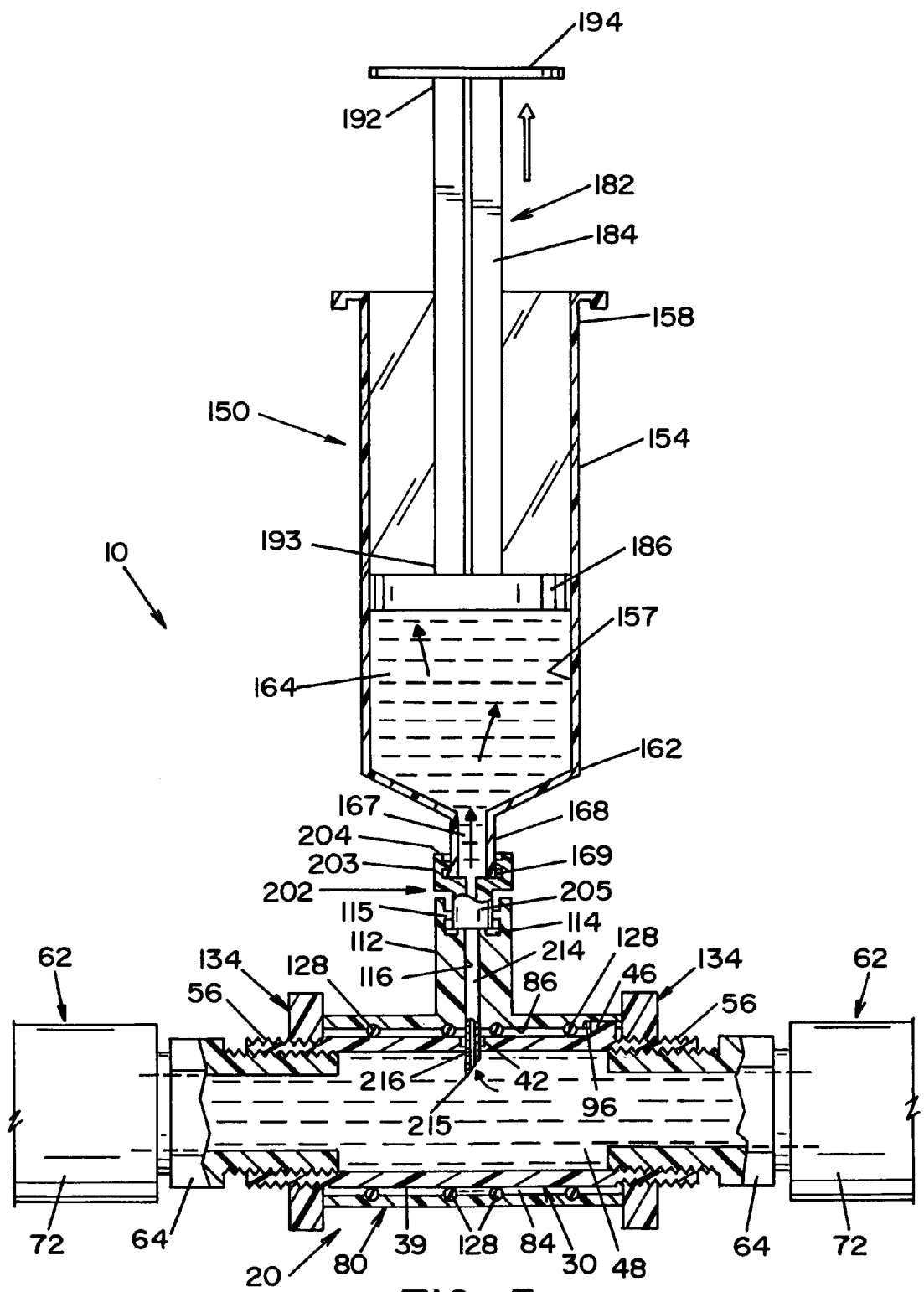
FIG. 5 is a sectional view of the sterile sampling assembly showing a sample being withdrawn from a process conduit.

Referring now to FIGS. 1, 4, and 5, syringe 150 is best seen therein. Syringe 150 includes a barrel 154. Barrel 154 is generally cylindrical in shape and has an open end 158, a closed end 162, and an inner surface 157 that together define an expandable chamber 164. A tubular nipple 168 is formed at closed end 162. Nipple 168 defines a passageway 167 that fluidly communicates with chamber 164. Nipple 168 includes a surface means 169 defined thereon that is dimensioned to engage needle 202. In the embodiment shown, surface means 169 is a male Luer-Lok® fitting.

Needle 202 includes a base portion 203 that is dimensioned to matingly engage with nipple 168. Base portion 203 has a first end 204 dimensioned to matingly engage surface means 169 of nipple 168. Base portion 203 has a second end 205 dimensioned to matingly engage annular recess 114 of boss 112. In one embodiment, second end 205 is dimensioned as a male Luer-Lok® fitting. Second end 205 is also dimensioned to matingly engage a needle cover (not shown), as is conventionally known. Needle 202 has a hollow shaft 214 that extends from second end 205 of base portion 203. Hollow shaft 214 has a distal end 215. Hollow shaft 214 defines a passageway 216 therethrough that fluidly communicates with chamber 164 when first end 204 is engaged with surface means 169.

A plunger 182 is disposed in chamber 164 of barrel 154. Plunger 182 has an elongated shaft 184 that has a first end portion 192 and a second end portion 193. First end portion 192 is formed to define a thumb/finger engaging portion 194. Second end portion 193 is formed to define a piston to be received within barrel 154. Piston 186 is dimensioned to sealingly engage inner surface 157 of barrel 154 and to allow movement of shaft 184 relative to barrel 154.

In one embodiment, core 30, coupling 62, and housing 80 are formed of a polymeric material such as, by way of example and not limitation, polypropylene, fluoropolymer, polyvinyl chloride (PVC), or a combination thereof. Syringe 150 is formed of conventionally known materials.

Device 10, as heretofore described, is preferably sold as a kit including body assembly 20 and syringe 150, such that assembly of these two components by the user is required. Body assembly 20 is comprised of core 30 and housing 80 assembled together. In a preferred embodiment, body assembly 20 includes cap 118 and boss 112 engaged together by surface engaging means 115 and surface means 121. Additionally, couplings 62 are attached to both ends of core 30. Thus device 10 is provided as a partially assembled kit and the user is required only to install assembly 20 in conduit 12 and then to attach syringe 150 to the housing 80 as will be discussed below.

The components of device 10 are preferably produced in a sterile manner, or sterilized prior to packaging, to be provided to a user in sterile packaging. It is appreciated that assembly 20 will be handled by the end user in accordance with sterile practices. By way of example and not limitation, such sterile practices can include: removal of assembly 20 and syringe 150 from the sterile packaging by a user wearing sterile rubber gloves, cleaning of the ends of conduit 12 prior to installation of assembly 20, and removal of cap 118 immediately prior to attachment of syringe 150 to assembly 20.

The present invention shall now be further described with respect to the operation of sterile sampling device 10. As discussed above, a typical reprocessing treatment cycle consists of a treatment/decontamination cycle or cycles using a decontaminating or sterilizing solution followed by a rinse cycle or cycles using sterile water. Whether a decontamination process is successful may be determined by assessing the degree to which any biological activity is apparent in the rinse water. A sample of the rinse water may be obtained using sterile sampling device 10.

Figure 3:
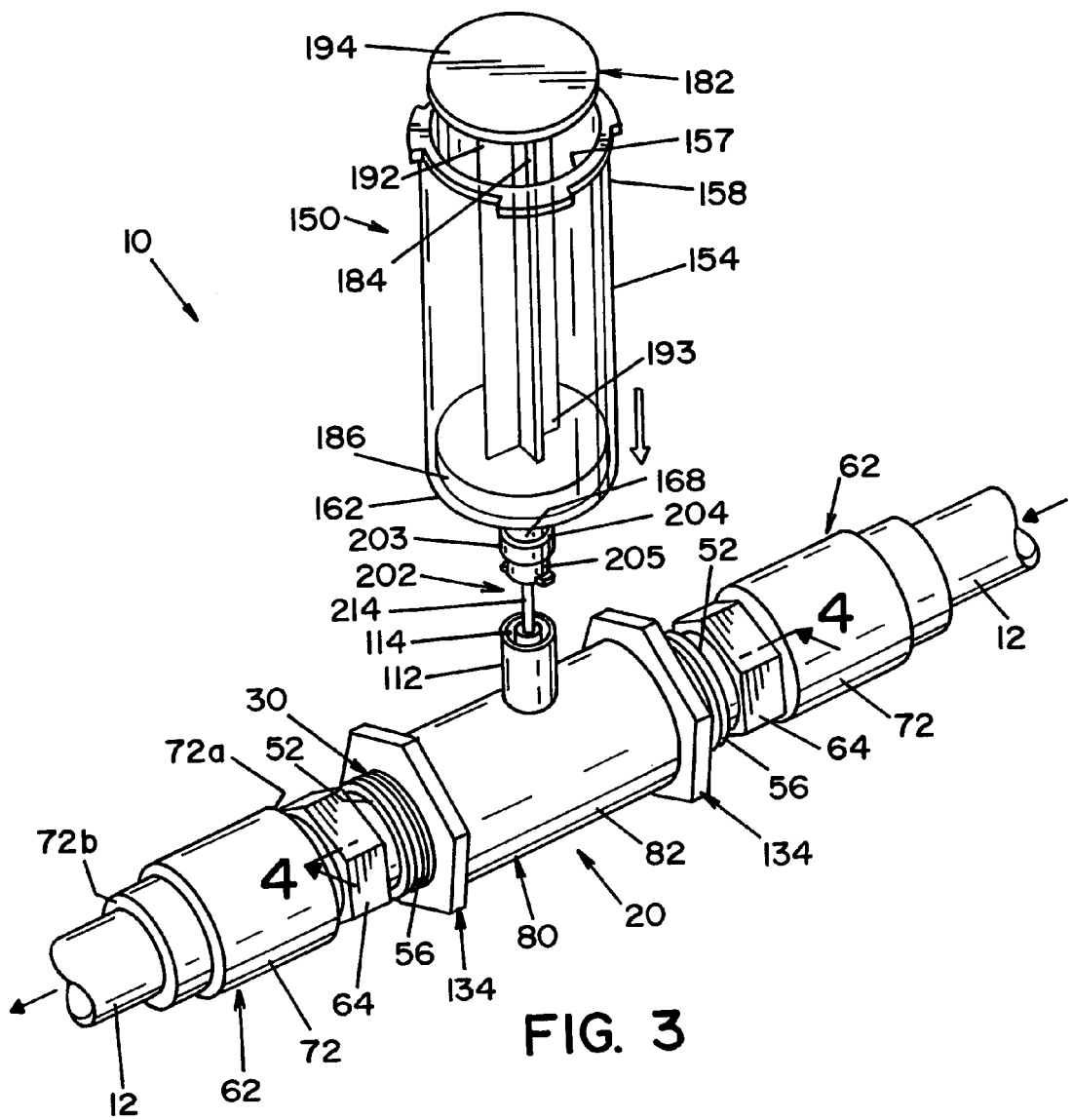
FIG. 3 is a perspective view illustrating the sterile sampling assembly attached to a process conduit, and illustrating a syringe being attached to a body that is installed in a process conduit.

Referring now to FIGS. 1, 3, 4, and 5, use of sterile sampling device 10 includes the following steps. First, assembly 20 is attached to two spaced apart portions of conduit 12 by couplings 62. Conduit 12 is part of a sterilization system or apparatus and is dimensioned to contain a sterilizing or washing fluid. Next, a reprocessing treatment cycle is conducted and is followed by at least one rinse cycle. When assembly 20 is installed in conduit 12, the sterilant flowing through conduit 12 will insure sterility of first passageway 48 of core 30. Then cap 118 is removed from boss 112. FIG. 2 shows a typical installation. As shown, cap 118 is preferably engaged with boss 112. After cap 118 is removed from boss 112, syringe 150 is attached to housing 80 at boss 112. As shown in FIG. 3, as syringe 150 is attached to housing 80, shaft 214 of needle 202 is inserted through bore 116. Sterile packaging and sterile handling procedures mentioned above insure the sterility of needle 202 as it penetrates into first passageway 48. Distal end 215 of shaft 214 penetrates recess 42 of core 30 and second end 205 of base portion 203 is engaged with boss 112.

During a rinse cycle, a sample is withdrawn from conduit 12. The sample is preferably withdrawn from conduit 12 during the last rinse cycle. To this end, plunger 182 is drawn away from closed end 162 thereby expanding chamber 164. The process fluid, i.e. rinse water, is drawn through passageway 216 and passageway 167 into expandable chamber 164. When the desired amount of process fluid has been collected within expandable chamber 164, syringe 150 is left in place. After completion of the rinse cycle(s), conduit 12 is drained of process fluid. When conduit 12 is free of fluid, syringe 150 is removed from housing 80 with the fluid sample contained within expandable chamber 164. The fluid sample is transferred directly to test media and incubated. The test media is incubated at a specific temperature for a predetermined amount of time. After incubation, the sample is evaluated for the presence of biological activity. If biological activity is present on the test media, the level of biological activity is assessed and compared to a predetermined standard to determine whether the decontamination cycle was effective. Finally, assembly 20 is removed from conduit 12 and replaced with an unused assembly 20 prior to beginning a subsequent treatment cycle.

In the embodiment described, device 10 is provided as assembly 20 and syringe 150. It is appreciated that device 10 can be provided as a kit of unassembled parts. Alternately, device 10 can be provided completely assembled such that syringe is 150 attached to assembly 20 upon delivery to the end user. In such an embodiment, the end user would connect system 10 to conduit 12. One skilled in the art would recognize that system 10 can be provided assembled to any degree between the two extremes just mentioned.

As described above, a sterile sampling device 10 is provided that can be inserted in a process conduit that is part of a medical washer, sterilization device, or other processing device where sterile extraction of sterile samples is required. Device 10 is replaceable within conduit 12. In this manner, a high degree of sterility may be maintained. Replacing a previously used device 10 with a new sterile device 10 allows the user to reduce the possibility of contamination due to poor or inadequate cleaning of a sampling device between uses. Preferably, a user of device 10 replaces it with a new device 10 after one use. By doing so, the user will continue to insure the sterility of process conduit 12 and samples taken therefrom.

While the present invention is described herein with reference to withdrawing a sterile sample from a process conduit, pipe, or tubing; it should be appreciated that the present invention finds utility in withdrawing samples from other types of fluid containers in sterile and non-sterile environments. Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. An apparatus for obtaining a sample of fluid from a process conduit, said apparatus comprising:
a tubular core having a passageway extending axially therethrough, said tubular core having ends that attach to spaced-apart portions of a conduit;
a tubular sleeve surrounding said tubular core wherein said tubular core extends axially through said tubular sleeve, said tubular sleeve having a bore extending radially through a side wall of said tubular sleeve, said bore fluidly communicating with said tubular core; and
a syringe mountable to said sleeve, said syringe having a needle dimensioned to extend axially through said bore to puncture a side wall of said tubular core and to project into said passageway inside said tubular core.

2. An apparatus as defined in claim 1, wherein said bore is in a predetermined position relative to said core.

3. An apparatus as defined in claim 1, wherein said tubular core has a defined area thereon, said defined area being dimensioned to facilitate puncturing said tubular core.

4. An apparatus as defined in claim 3, wherein said bore is aligned with said defined area.

5. An apparatus for obtaining a sample of fluid from a process conduit, said apparatus comprising:
a tubular core having a passageway extending therethrough, said tubular core having ends attachable to spaced-apart portions of a conduit;
a tubular sleeve surrounding said tubular core wherein said tubular core extends lengthwise through said tubular sleeve, said tubular sleeve having a bore extending therethrough, said bore fluidly communicating with said tubular core; and
a syringe mountable to said sleeve, said syringe having a needle dimensioned to extend through said bore to puncture said tubular core and to project into said passageway inside said tubular core, wherein a boss is formed on said tubular sleeve and said bore is formed through said boss and a cap attached to said boss, to seat in said bore of said boss.

6. An apparatus as defined in claim 5, wherein said boss has a distal end and said distal end has an annular recess having a surface engaging means formed therein.

7. An apparatus as defined in claim 6, wherein said syringe has a needle having a base portion, said base portion being dimensioned to engage said surface engaging means.

8. An apparatus as defined in claim 6, wherein said surface engaging means is dimensioned to receive said syringe.

9. An apparatus for obtaining a sample of fluid from a process conduit, said apparatus comprising:
a tubular core having a passageway extending therethrough, said tubular core having ends attachable to spaced-apart portions of a conduit;
a tubular sleeve surrounding said tubular core wherein said tubular core extends lengthwise through said tubular sleeve, said tubular sleeve having a bore extending therethrough, said bore fluidly communicating with said tubular core; and
a syringe mountable to said sleeve, said syringe having a needle dimensioned to extend through said bore to puncture said tubular core and to project into said passageway inside said tubular core,
wherein said tubular core has a defined area thereon, said defined area being dimensioned to facilitate puncturing said tubular core, said bore is aligned with said defined area, and said tubular core has an outer surface having a rectangular projection formed at one end of said tubular core.

10. An apparatus as defined in claim 9, wherein said tubular sleeve has an inner wall, said inner wall having a rectangular recess formed at one end thereof, wherein said rectangular recess is dimensioned to receive said rectangular projection of said tubular core.

11. An apparatus for obtaining a sample of fluid from a process conduit, said apparatus comprising:

a tubular core having a passageway extending therethrough, said tubular core having ends attachable to spaced-apart portions of a conduit;

a tubular sleeve surrounding said tubular core wherein said tubular core extends lengthwise through said tubular sleeve, said tubular sleeve having a bore extending therethrough, said bore fluidly communicating with said tubular core; and a syringe mountable to said sleeve, said syringe having a needle dimensioned to extend through said bore to puncture said tubular core and to project into said passageway inside said tubular core, wherein said tubular sleeve has an inner wall, said inner wall being dimensioned to receive a plurality of o-rings.

12. An apparatus as defined in claim 11, wherein said plurality of o-rings are dimensioned to sealingly engage said inner wall of said tubular sleeve and said tubular core.

* * * * *